US011246624B2

(12) United States Patent
Grutta et al.

(10) Patent No.: US 11,246,624 B2
(45) Date of Patent: Feb. 15, 2022

(54) BROACH HOLDER TOOL WITH REDUCED RASP MOMENT

(71) Applicant: Joint Development, LLC, Salt Lake City, UT (US)

(72) Inventors: James T. Grutta, Draper, UT (US); Dermott J. McHugh, Seattle, WA (US); Chris A. Weaber, Sandy, UT (US)

(73) Assignee: Joint Development, LLC, Salt Lake City, UT (US)

( * ) Notice: Subject to any disclaimer, the term of this patent is extended or adjusted under 35 U.S.C. 154(b) by 789 days.

(21) Appl. No.: 15/345,379

(22) Filed: Nov. 7, 2016

(65) Prior Publication Data

US 2017/0128097 A1 May 11, 2017

Related U.S. Application Data (60) Provisional application No. 62/252,157, filed on Nov. 6, 2015.

(51) Int. Cl.
*A61B 17/3207* (2006.01)
*A61B 17/16* (2006.01)
*A61B 17/32* (2006.01)

(52) U.S. Cl.
CPC .. *A61B 17/320725* (2013.01); *A61B 17/1659* (2013.01); *A61B 2017/320008* (2013.01)

(58) Field of Classification Search
CPC ...... A61B 17/1659–1693; A61B 17/32; A61B 17/14; A61B 17/320725; B25G 3/28; B25G 3/04

USPC .......... 606/79–85, 95, 62, 99-100
See application file for complete search history.

(56) References Cited

U.S. PATENT DOCUMENTS

| | | | | | |
|---|---|---|---|---|---|
| 4,306,550 | A | * | 12/1981 | Forte ............. | A61B 17/1659 30/276 |
| 4,587,964 | A | * | 5/1986 | Walker ........... | B25G 3/16 606/85 |
| 5,089,003 | A | * | 2/1992 | Fallin ............ | A61B 17/1659 606/53 |
| 5,443,471 | A | * | 8/1995 | Swajger ......... | A61B 17/1659 606/99 |
| 5,720,750 | A | * | 2/1998 | Koller ............ | A61F 2/4684 606/85 |
| 6,205,884 | B1 | * | 3/2001 | Foley ............ | A61B 17/1659 74/544 |
| D549,329 | S | * | 8/2007 | Aparici .......... | D24/133 |

(Continued)

OTHER PUBLICATIONS

De Geest, Direct Anterior Total Hip Arthroplasty, Acta Orthopaedica Belgica, vol. 79—Feb. 2013, pp. 166-173, Ostend, Belgium.

*Primary Examiner* — Jessica Weiss
(74) *Attorney, Agent, or Firm* — Lowry Blixseth APC; Scott M. Lowry (57) ABSTRACT

The broach or rasp holder tool with reduced rasp moment includes an angled strike plate with an optional curved or spheroidal surface and/or an angled withdrawal plate having a contact surface for receiving a generally perpendicular strike force that generally aligns with a point along a rasp for substantially eliminating a moment applied thereto while broaching the intramedullary canal in preparation for implanting a prosthetic stem during joint replacement surgery.

20 Claims, 9 Drawing Sheets

(56) References Cited

U.S. PATENT DOCUMENTS

| | | | | |
|---|---|---|---|---|
| 7,935,125 B2* | 5/2011 | Bastian | | A61B 17/1659 |
| | | | | 606/99 |
| 8,262,668 B2* | 9/2012 | Biegun | | A61B 17/1668 |
| | | | | 606/99 |
| 8,337,502 B2* | 12/2012 | Bastian | | A61F 2/4607 |
| | | | | 606/86 R |
| 8,657,824 B2* | 2/2014 | Sharp | | A61B 17/1604 |
| | | | | 606/84 |
| 9,456,810 B2* | 10/2016 | Rister | | A61B 17/1659 |
| 9,796,074 B2* | 10/2017 | Mugnier | | B25G 3/04 |
| 9,814,529 B2* | 11/2017 | Dmuschewsky | | A61B 90/50 |
| 2005/0288676 A1* | 12/2005 | Schnieders | | A61B 17/1668 |
| | | | | 606/79 |
| 2006/0111725 A1* | 5/2006 | Biegun | | A61B 17/1659 |
| | | | | 606/85 |
| 2007/0233134 A1* | 10/2007 | Bastian | | A61B 17/1659 |
| | | | | 606/85 |
| 2008/0255565 A1* | 10/2008 | Fletcher | | A61B 17/1659 |
| | | | | 606/80 |
| 2010/0121331 A1* | 5/2010 | Sharp | | A61F 2/4607 |
| | | | | 606/80 |
| 2010/0331994 A1* | 12/2010 | Surma | | A61F 2/4607 |
| | | | | 623/23.15 |
| 2012/0071862 A1* | 3/2012 | Burgi | | A61B 17/1659 |
| | | | | 606/1 |
| 2012/0083769 A1* | 4/2012 | Burgi | | A61F 2/4607 |
| | | | | 606/1 |
| 2012/0136392 A1* | 5/2012 | Keegan | | A61B 17/7059 |
| | | | | 606/249 |
| 2013/0090657 A1* | 4/2013 | Bastian | | A61F 2/4607 |
| | | | | 606/79 |
| 2013/0197489 A1* | 8/2013 | Rister | | A61B 17/1668 |
| | | | | 606/1 |
| 2014/0121650 A1* | 5/2014 | Thomsen | | A61B 17/1659 |
| | | | | 606/1 |
| 2014/0207200 A1* | 7/2014 | Kerboul | | A61B 17/1659 |
| | | | | 606/86 R |
| 2016/0059403 A1* | 3/2016 | Mugnier | | A61B 17/1668 |
| | | | | 16/422 |
| 2017/0367714 A1* | 12/2017 | McCulloch | | A61F 2/4607 |

* cited by examiner

BROACH HOLDER TOOL WITH REDUCED RASP MOMENT

BACKGROUND OF THE INVENTION

The present invention generally relates to a rasp or broach holder tool with reduced rasp moment for use during joint replacement surgery. More specifically, the present invention relates to a rasp or broach holder tool having a strike plate and/or a withdrawal plate angularly aligning a rasp to reduce or eliminate the moment at the point of rasp insertion and/or removal, respectively, when broaching or rasping the intramedullary canal in preparation for implantation of a prosthetic femoral stem during total hip replacement surgery.

Advancements in surgery have enhanced the feasibility of performing total joint replacement surgery, such as for the knee, hip, or shoulder, to replace natural joints that may need restoration as a result of disease or injury. For example, with respect to total hip replacement surgery, it is necessary to replace the acetabulum and femoral head with a prosthetic acetabular cup and insert, and femoral stem having an artificial femoral head sized for engagement with the acetabular cup and insert assembly. Total hip replacement surgery typically involves dislocating the femur, resecting the femoral neck, reaming the acetabulum in preparation to receive the acetabular cup, and rasping the intramedullary canal to form a shaft or channel therein suitable to receive a prosthetic femoral stem having a head thereon sized for engagement with the acetabular cup. A tool called a broach or rasp is used to contour the intramedullary canal so that the channel walls are approximately the size and shape of the overall geometry of the appropriately sized prosthetic femoral stem to ensure that the implant has a more accurate and precise fit during implantation.

There are several surgical techniques known in the art for performing total hip replacement surgery. One such traditional surgical technique is a posterior approach whereby the patient is positioned on his or her side and the surgeon makes an approximately 3-6 inch incision along the rear of the body near the gluteus maximus. Here, the gluteus maximus muscle is split and requires repair during wound closure. This method provides excellent exposure to the acetabulum and femur, but has drawbacks related to dislocation and leg-length inequality. An alternative approach is an anterior approach whereby the patient lays on his or her back and the surgeon makes an approximately 3-6 inch incision along the front or side of the upper thigh. One drawback of the anterior approach is that the femur fracture rate tends to be higher when compared to the aforementioned posterior approach.

As briefly mentioned above, in most cases, surgeons use a broach or rasp to open and size the intramedullary canal for preparation to receive the femoral stem implant. This may be accomplished through the use of rasps that vary in size and shape and that can be interchanged using the broach holder during surgery to attain the desired channel. In this respect, the surgeon may start with a smaller size rasp to open the channel, and then use progressively larger rasps (e.g., one or more) until the final rasp corresponds approximately to the size of the femoral prosthesis. The rasp typically includes a series of teeth to cut away the bone during insertion and removal. One of the complications that may occur during total hip replacement is an intraoperative proximal femoral fracture. The risk of these fractures has been shown to increase with the use of offset broaching tools, likely due to the non-axial forces created by the strike plate on the broach holder being offset from the central axis of the broach during impaction into the femur. Intraoperative fractures may occur during the broaching process, or during the femoral stem implantation, and postoperative fracture could occur in the weeks following hospital discharge. While the broach holder cannot directly affect forces during stem implantation, or postoperatively, the increased stresses created during broaching may weaken the bone and contribute to the increased risk of fracture even during stem implantation, or postoperatively. Intraoperative fracture increases the incidence of complication, causes additional pain, and potentially creates a significant surgical delay and/or cost to the procedure.

Broach holder tools often include a curved or offset section that helps facilitate angled insertion to more accurately access the intramedullary canal, especially when performing an anterior approach. The broach holder may be straight or offset depending upon surgeon preference or approach, but the anterior approach generally prohibits such axial insertion of the broach for purposes of rasping the intramedullary canal. When using an angled broach holder tool, as opposed to a straight broach holder tool, non-axial forces are introduced to the intramedullary canal to attain adequate rasping of the canal. These non-axial forces propagate through the rasp and may create microfractures in the bone, which may lead to femur fracture. This is because the bone at the site of rasp entry into the canal may be over stressed as a result of the increased moment applied to the broach holder and rasp. Thus, a broach holder tool and rasp used for the preparation of the intramedullary canal for receiving a femoral stem implant prosthesis that includes any appreciable offset from the centerline of the rasp can greatly increase the chances of bone fracture while rasping during surgery. Microfracture may also lead to fracture postoperatively in the weeks following surgery as the patient begins to weight-bear and become more active.

Figure 1:
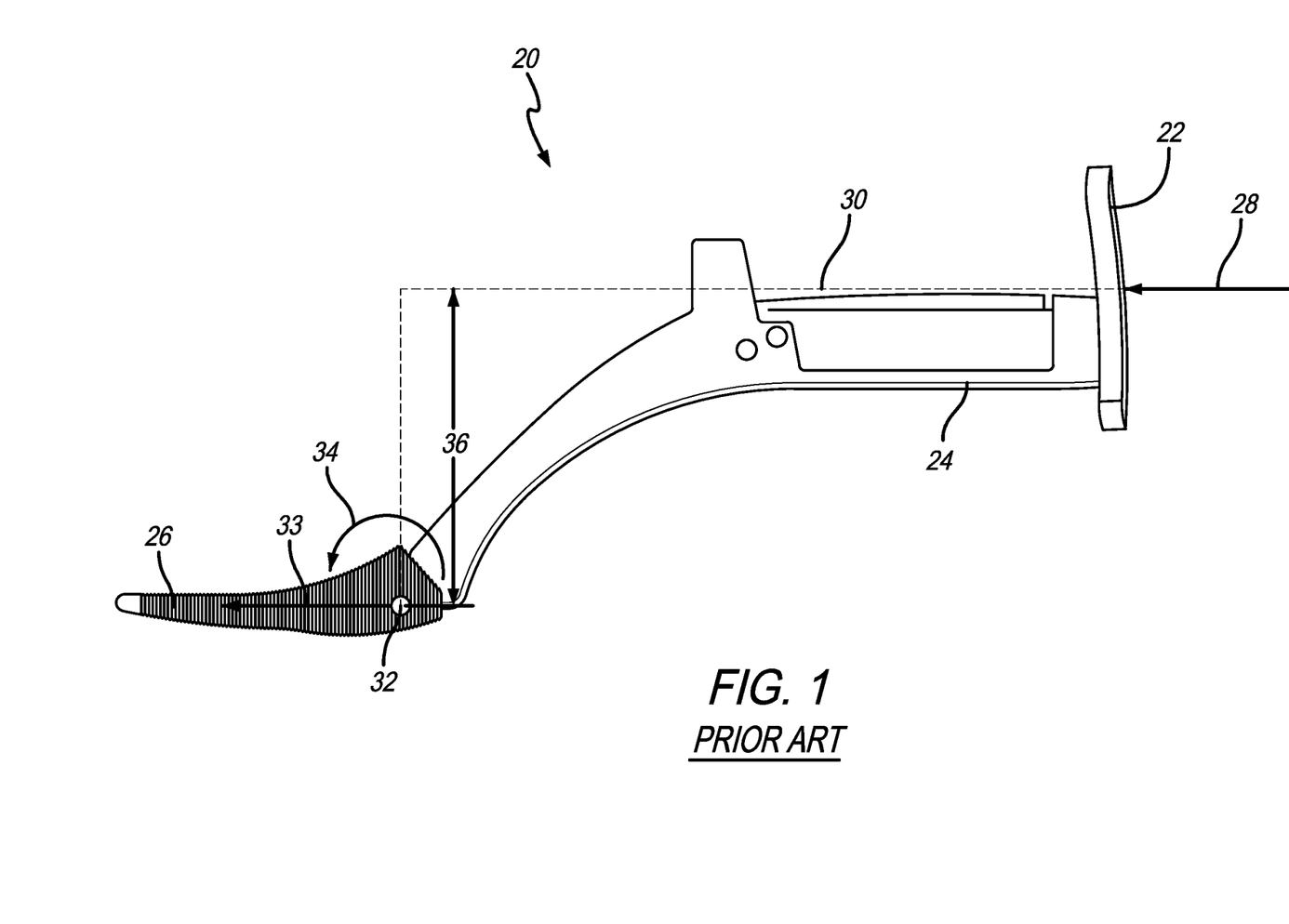
FIG. 1 is a side perspective view of a prior art broach holder tool including a strike plate perpendicular to a rasp, and illustrating creation of a moment at the rasp when applying a force at the strike plate.
Figure 2:
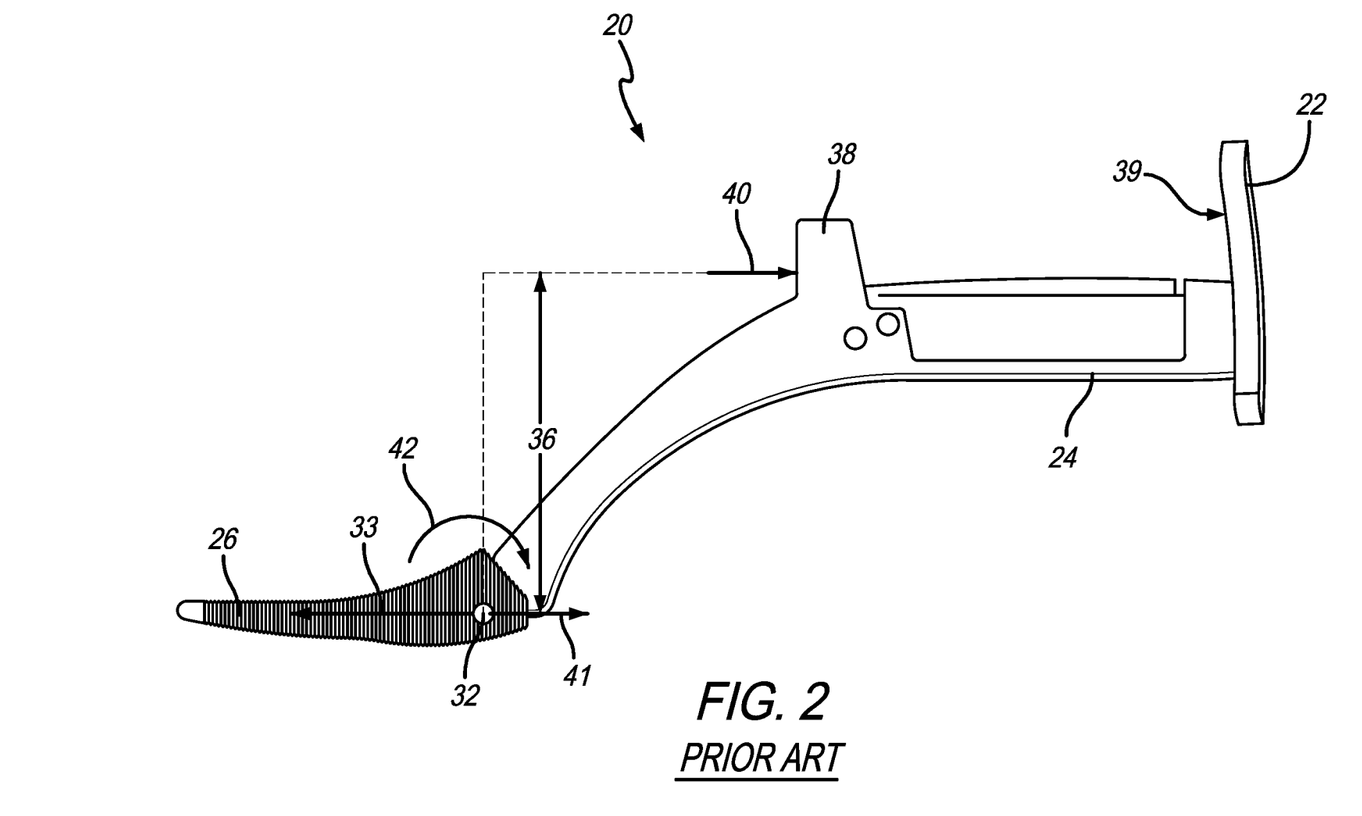
FIG. 2 is a side perspective view of the prior art broach holder tool of FIG. 1, illustrating creation of a moment at the rasp when applying a force at a withdrawal plate or a back side of the strike plate.

In this respect, FIGS. 1 and 2 illustrate a prior art broach holder tool 20 that includes a strike plate 22 at one end of a section 24 having a rasp 26 attached thereto at an opposite end thereof. The section 24 is shown having a general "S"-shape such that the strike plate 22 resides at a point above the location where the rasp 26 attaches to the section 24. Application of a strike force 28 on the strike plate 22, e.g., by way of a hammer or other tool that may be used during surgery to further depress the rasp 26 into the intramedullary canal, generates a general forward force along the direction indicated by a dotted force line 30. This force line 30 is offset from a point 32 where the rasp 26 attaches to the section 24. As a result, application of the force 28 acts as both an axial force 33 and a moment 34 about the point 32, or a commensurate point along the length of the rasp 26 where the rasp 26 may engage or encounter resistance within the intramedullary canal during rasping. The axial force 33 is approximately equal to the strike force 28 and is the desired force for broaching the femur. The moment can be calculated as $M=(F)(D)$, where M is equal to the moment 34, F is equal to the strike force 28 and D is equal to a distance 36 generally defined as between the horizontal force line 30 and point 32 (i.e., the moment arm). During broaching, this moment 34 must be resisted by reaction forces within the femur. Those forces reduce the effectiveness of the axial force 33 to move the broach more deeply within the femur in an axial path, and also create internal hoop stresses within the proximal femur. Bone has good natural compressive strength, but poor strength in tension. Accordingly, bone is relatively strong at absorbing stresses along its length, but not perpendicular thereto.

Therefore, hoop stresses should be avoided. This situation also forces the surgeon to push the broach holder down to maintain proper alignment of the broach and to use higher strike forces to overcome the extra resistance. Therefore, it is unsurprising that there is an increased occurrence of proximal fractures when using the prior art broach holder tool using the anterior approach, as described above.

The same issue applies when attempting to remove the prior art broach holder tool 20 by way of striking a withdrawal plate 38 or a back side 39 of the main strike plate 22, as shown in FIG. 2. Here, the withdrawal plate 38 is similarly parallel to the strike plate 22, generally perpendicular to the section 24, and offset from the rasp 26. Application of a withdrawal force 40 on the withdrawal plate 38 creates both an axial force 41, and a withdrawal moment 42 that attempts to rotate or pivot the rasp 26 in the clockwise direction as indicated by the moment 42. The moment 42 applied to the rasp 26 increases the resistance during extraction of the rasp 26 due to the reaction forces within the femur. This requires the surgeon to use an increased withdrawal force 40 to remove the rasp 26.

Figure 3A:
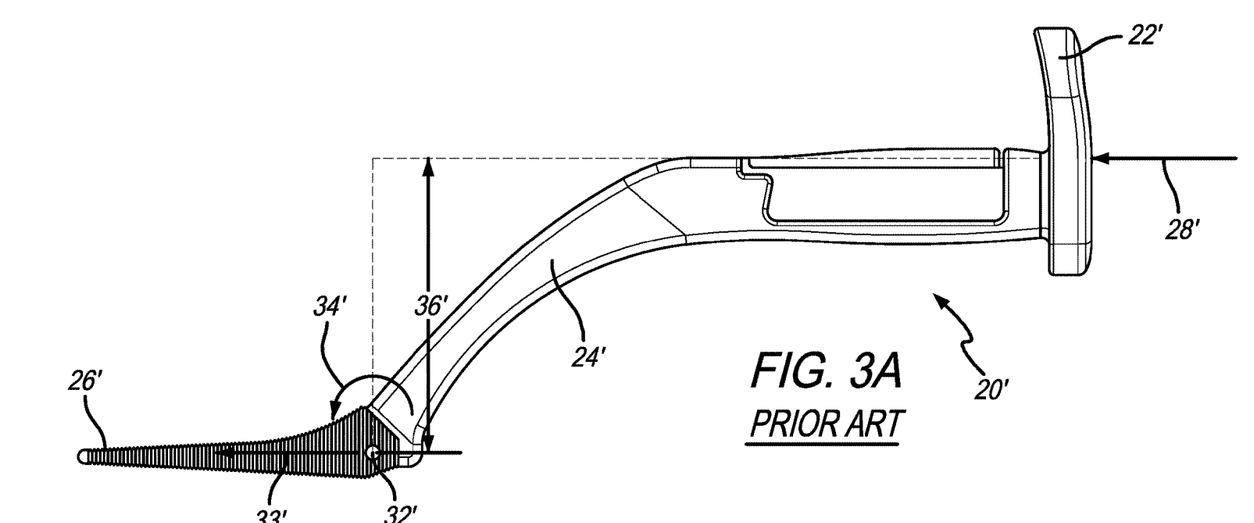
FIG. 3A is a side perspective view of an alternative prior art broach holder tool incorporating a vertically and horizontally offset strike plate.
Figure 3B:
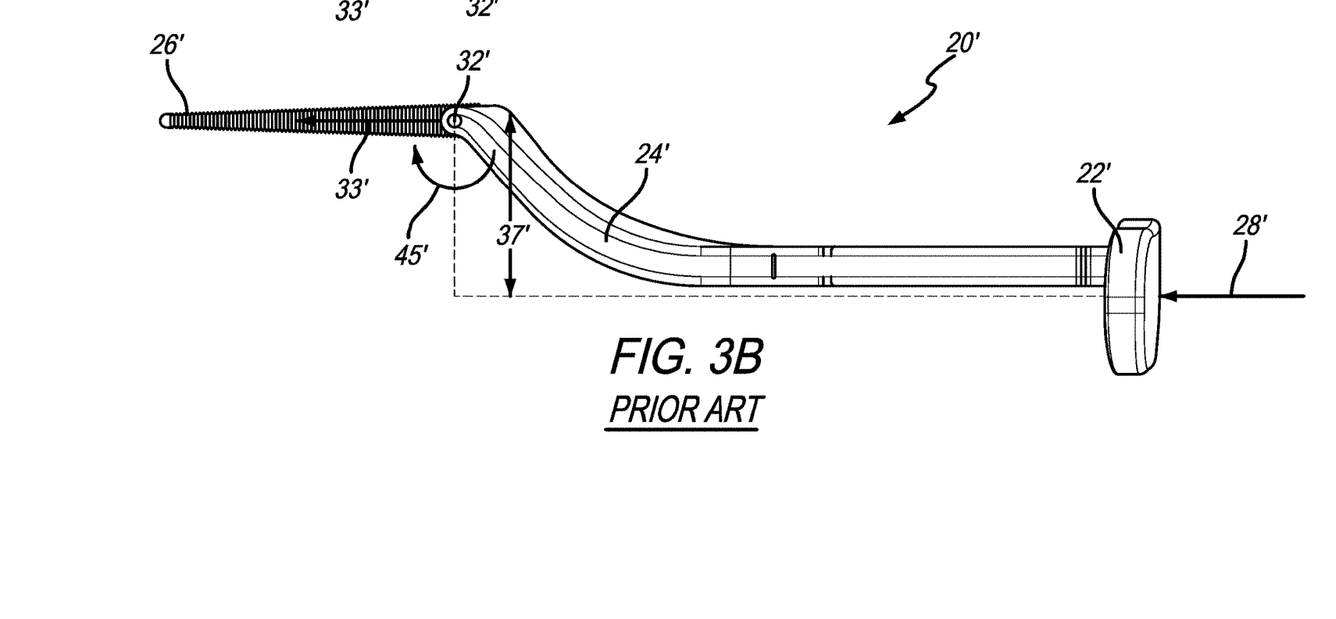
FIG. 3B is a top perspective view of the alternative prior art broach holder tool of FIG. 3A.

In another example, FIGS. 3A and 3B illustrate an alternative prior art broach holder tool 20' that includes a section 24' that positions the strike plate 22' at a vertical distance above the rasp 26' (e.g., as described above with respect to FIGS. 1 and 2), as shown in FIG. 3A, and a horizontal distance to the side of the rasp 26', as shown in FIG. 3B. When the strike plate 22' is impacted with a strike force 28', the strike force 28' is offset from the point 32' by a vertical distance 36' and a horizontal distance 37'. This respectively creates two moments, a first moment 34' (FIG. 3A) and a second moment 45' (FIG. 3B), as a result of the "S" curved section 24'. During broaching, the above-identified problem is only exacerbated by the two moments 34', 45' that must be resisted by even more reaction forces within the femur. Those resistive forces reduce the effectiveness of the strike force 28' to move the broach more deeply within the femur in an axial path (e.g., along an axial force 33') and also create internal hoop stresses within the proximal femur. This only increases the risk of proximal femur fractures during broaching and makes it more difficult to control alignment of the broaching tool.

There exists, therefore, a significant need in the art for a broach holder that reduces or eliminates the applied moments through the rasp which may cause unintended internal stresses within the intramedullary canal during surgery. The effect of this reduction in applied moments will substantially reduce or limit the internal hoop stresses in the proximal femur. The present invention fulfills these needs and provides further related advantages.

SUMMARY OF THE INVENTION

One embodiment of the broach holder tool with reduced rasp moment as disclosed herein includes a generally elongated and rigid S-shaped broach holder body having a size and shape for broaching a bone. A selectively interchangeable rasp for broaching the bone may be selectively coupled to one end of the broach holder body. Furthermore, an angled strike plate may be coupled to another portion of the broach holder body and have a strike surface for selectively receiving a strike force perpendicular thereto that translates along an angled directional strike line extending through the rasp substantially near a drive point where the rasp enters the bone. This substantially reduces the rasp moment at the point where the rasp enters the intramedullary canal, while simultaneously permitting sufficient translation of a substantially horizontal or insertion force that permits broaching the intramedullary canal.

In one aspect of this embodiment, the angled directional strike line may extend through the rasp at a maximum offset of 10 degrees from the drive point. This permits continued substantial alignment of the angled directional strike line with the drive point, as the drive point may change during the rasping or broaching process in view that the rasp moves into and out from the intramedullary canal. Additionally, the angled strike plate may include a vertical offset angle $\alpha$ between 10-30 degrees, which is defined by the formula: $\alpha=90-\arctan(X/Y)$, where X is the horizontal distance between the drive point and where the strike force contacts the strike surface of the angled strike plate and Y is the vertical gain between the drive point and where the strike force contacts the strike surface of the angled strike plate. Decreasing the vertical gain may decrease the vertical offset angle $\alpha$ and increasing the vertical gain may increase the vertical offset angle $\alpha$. Changing the gain may affect a substantially horizontal insertion force applied at the rasp, i.e., the substantially horizontal insertion force at the rasp may increase by decreasing the vertical gain and the substantially horizontal insertion force at the rasp may decrease by increasing the vertical gain, all while substantially maintaining the reduced rasp moment.

In another aspect of this embodiment, the broach holder tool with a reduced rasp moment may include an angled withdrawal plate coupled to the broach holder body between the rasp and the angled strike plate. The angled withdrawal plate may include a withdrawal surface for selectively receiving a withdrawal force perpendicular thereto that translates substantially along an angled directional withdrawal line extending through a withdrawal point where the rasp is removed from the bone after broaching. Here, the angled withdrawal plate may include a vertical offset angle $\beta$ defined by the formula: $\beta=90-\arctan(A/B)$, where A is the horizontal distance between the withdrawal point and where the withdrawal force contacts the withdrawal surface of the angled withdrawal plate and B is the vertical distance between the withdrawal point and where the withdrawal force contacts the withdrawal surface of the angled withdrawal plate.

In another aspect of this embodiment, the strike surface of the strike plate may include a non-planar strike surface selected from the group consisting of a curved strike surface, a spherical strike surface, or a spheroidal strike surface. Here, the angled directional strike line may vary across the non-planar strike surface, depending where along the non-planar strike surface the strike force is applied. This allows for varying the location of the angled directional strike line relative to the drive point to help ensure that the angled directional strike line extends through the rasp at a maximum offset of 10 degrees from the drive point. To this end, striking the non-planar strike surface to vary the angled directional strike line may also correspond with a different drive point location along the length of the rasp. Alternatively, the angled strike plate may include an adjustable angled strike plate selectively positionable relative to the drive point. Here, the angled strike plate may pivot relative to the broach holder body by a lock-step engagement.

Another embodiment of the broach holder tool with reduced rasp moment as disclosed herein may include a generally elongated and rigid broach holder body that has a size and shape to facilitate broaching of an intramedullary canal in a bone in preparation for implantation of a prosthetic femoral stem. In this embodiment, the broach holder body may include a selectively interchangeable rasp coupled to one end and an angled strike plate coupled to another end, opposite the rasp. The angled strike plate may include a strike surface positioned relative to a drive point near where the rasp enters the bone to translate a strike force applied perpendicular to the strike surface through the drive point. This may produce an axial insertion force into the intramedullary canal while substantially reducing or eliminating the rasp moment. In one embodiment, the angled strike plate may include a vertical offset angle α defined by the formula: α=90−arctan (X/Y), where X is the horizontal distance between the drive point and where the strike force contacts the strike surface of the angled strike plate and Y is the vertical gain between the drive point and where the strike force contacts the strike surface of the angled strike plate.

Moreover, the broach holder tool with reduced rasp moment of this embodiment may also include an angled withdrawal plate coupled to the broach holder body between the rasp and the angled strike plate. The angled withdrawal plate may include a withdrawal surface for selectively receiving a withdrawal force generally perpendicular thereto that translates substantially along an angled directional withdrawal line generally aligned with a withdrawal point along the rasp. This substantially reduces the rasp moment at the withdrawal point when removing the broach holder tool from the intramedullary canal in the bone. Since the point of contact between the rasp and the bone may vary during withdrawal, the angled directional withdrawal line may extend through the rasp at a maximum offset of 10 degrees from the withdrawal point. Although, alternatively, the angled withdrawal plate may include an adjustable angled withdrawal plate selectively positionable relative to the withdrawal point to track the varying location of the withdrawal point along the rasp during removal. Here, the angled withdrawal plate may pivot relative to the broach holder body by a lock-step engagement.

In another aspect of this embodiment, the angled withdrawal plate may include a vertical offset angle β that is between 10 and 30 degrees, and is defined by the formula: β=90−arctan (A/B), where A is the horizontal distance between the withdrawal point and where the withdrawal force contacts the withdrawal surface and B is the vertical distance between the withdrawal point and where the withdrawal force contacts the withdrawal surface. Another feature of this embodiment includes wherein the withdrawal surface of the angled withdrawal plate includes a non-planar withdrawal surface selected from the group consisting of a curved withdrawal surface, a spherical withdrawal surface, or a spheroidal withdrawal surface. Here, the angled directional withdrawal line varies across the non-planar withdrawal surface, depending where the withdrawal force strikes the non-planar withdrawal surface. This allows for changing the positioning of the angled withdrawal line relative to the rasp to track a varying withdrawal point along the length of the rasp as the rasp is removed from the intramedullary canal.

In another embodiment, the broach holder tool with a reduced rasp moment as disclosed herein includes a generally elongated and rigid broach holder body having a size and shape for broaching a bone, a rasp selectively coupled to one end of the broach holder body, an angled strike plate coupled to another portion of the broach holder body opposite the rasp and having a strike surface positioned at a vertical offset angle α of 10-30 degrees for selectively receiving a strike force perpendicular thereto that drives through the rasp at a maximum offset of 10 degrees from a drive point where the rasp enters the bone, and an angled withdrawal plate extending out from the broach holder body between the rasp and the angled strike plate and including a withdrawal surface for selectively receiving a withdrawal force generally perpendicular thereto that translates substantially along an angled directional withdrawal line generally aligned with a withdrawal point along the rasp.

Here, the vertical offset angle α may be defined by the formula: α=90−arctan (X/Y), where X is the horizontal distance between the drive point and where the strike force contacts the strike surface and Y is the vertical gain between the drive point and where the strike force contacts the strike surface. Moreover, the angled withdrawal plate may include a vertical offset angle β defined by the formula: β=90−arctan (A/B), where A is the horizontal distance between the withdrawal point and where the withdrawal force contacts the withdrawal surface and B is the vertical distance between the withdrawal point and where the withdrawal force contacts the withdrawal surface.

The broach holder body may be an S-shape and a decrease in the vertical gain may decrease the vertical offset angle α and increase a substantially horizontal insertion force at the rasp. Alternatively, increasing the vertical gain of the S-shaped broach holder body may increase the vertical offset angle α and decrease the substantially horizontal insertion force at the rasp. Alternatively, the strike surface of the strike plate and the withdrawal surface of the withdrawal plate may each include a non-planar surface selected from the group consisting of a curved surface, a spherical surface, or a spheroidal surface. Additionally, the angled strike plate may be an adjustable angled strike plate that pivots relative to the broach holder body by a lock-step engagement and may be selectively positionable relative to the drive point along a selectively interchangeable rasp.

In another embodiment, the broach holder tool with a reduced rasp moment may include a generally elongated and rigid broach holder body having a size and shape for broaching a bone, a rasp selectively coupled to one end of the broach holder body, an angled strike plate coupled to another portion of the broach holder body opposite the rasp and having a non-planar strike surface positioned at a vertical offset angle α of 10-30 degrees for selectively receiving a strike force perpendicular thereto that translates along an angled directional strike line extending through the rasp at a maximum offset of 10 degrees from a drive point where the rasp enters the bone, and an angled withdrawal plate extending out from the broach holder body between the rasp and the angled strike plate and including a non-planar withdrawal surface for selectively receiving a withdrawal force generally perpendicular thereto that translates substantially along an angled directional withdrawal line generally aligned with a withdrawal point along the rasp.

Here, the angled directional strike line may vary across the non-planar strike surface and the angled directional withdrawal line may vary across the non-planar withdrawal surface, depending where the respective strike force or withdrawal force is applied to the non-planar strike surface or the non-planar withdrawal surface. To this end, the non-planar strike surface may be selected from the group consisting of a curved strike surface, a spherical strike surface, or a spheroidal strike surface and the non-planar withdrawal surface may be selected from the group consisting of a curved withdrawal surface, a spherical withdrawal surface, or a spheroidal withdrawal surface. The angled strike plate and/or the angled withdrawal plate may pivot relative to the broach holder body by a lock-step engagement.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 4:
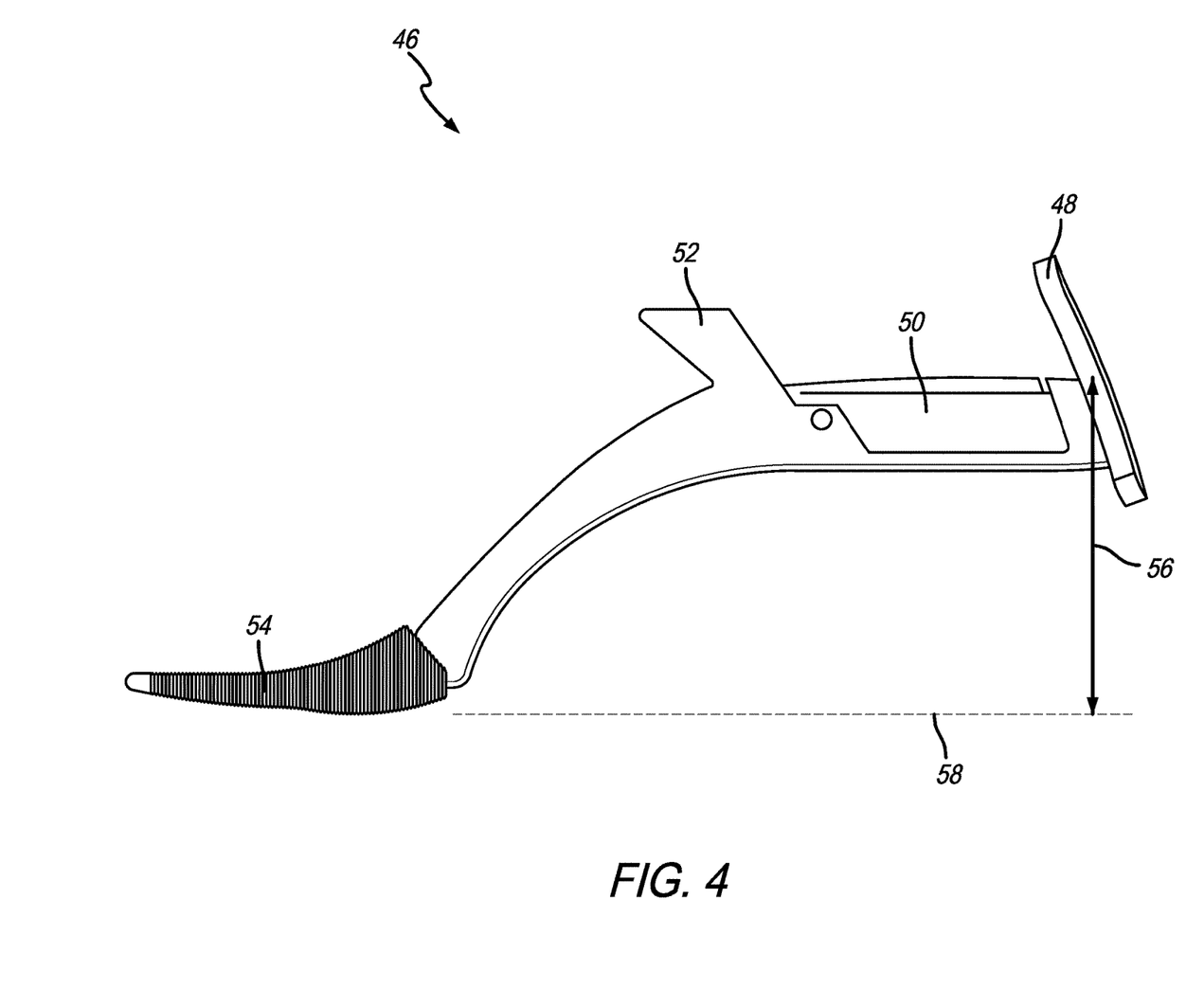
FIG. 4 is a side perspective view illustrating one embodiment of a broach holder tool with reduced rasp moment as disclosed herein.
Figure 5:
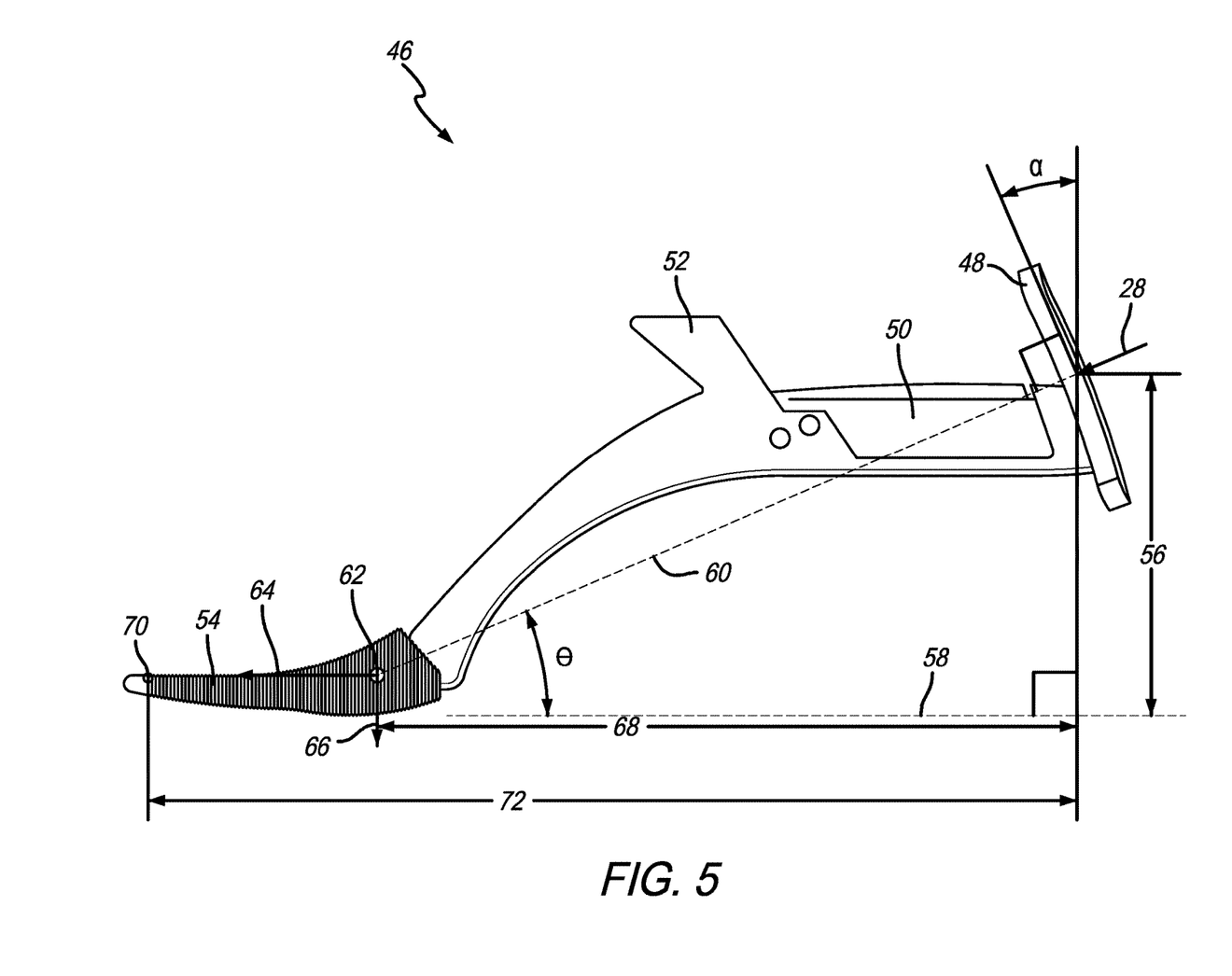
FIG. 5 is a side perspective view of the broach holder tool with reduced rasp moment similar to FIG. 4, further illustrating applying a force to the strike plate without substantial creation of a moment at the rasp.
Figure 6:
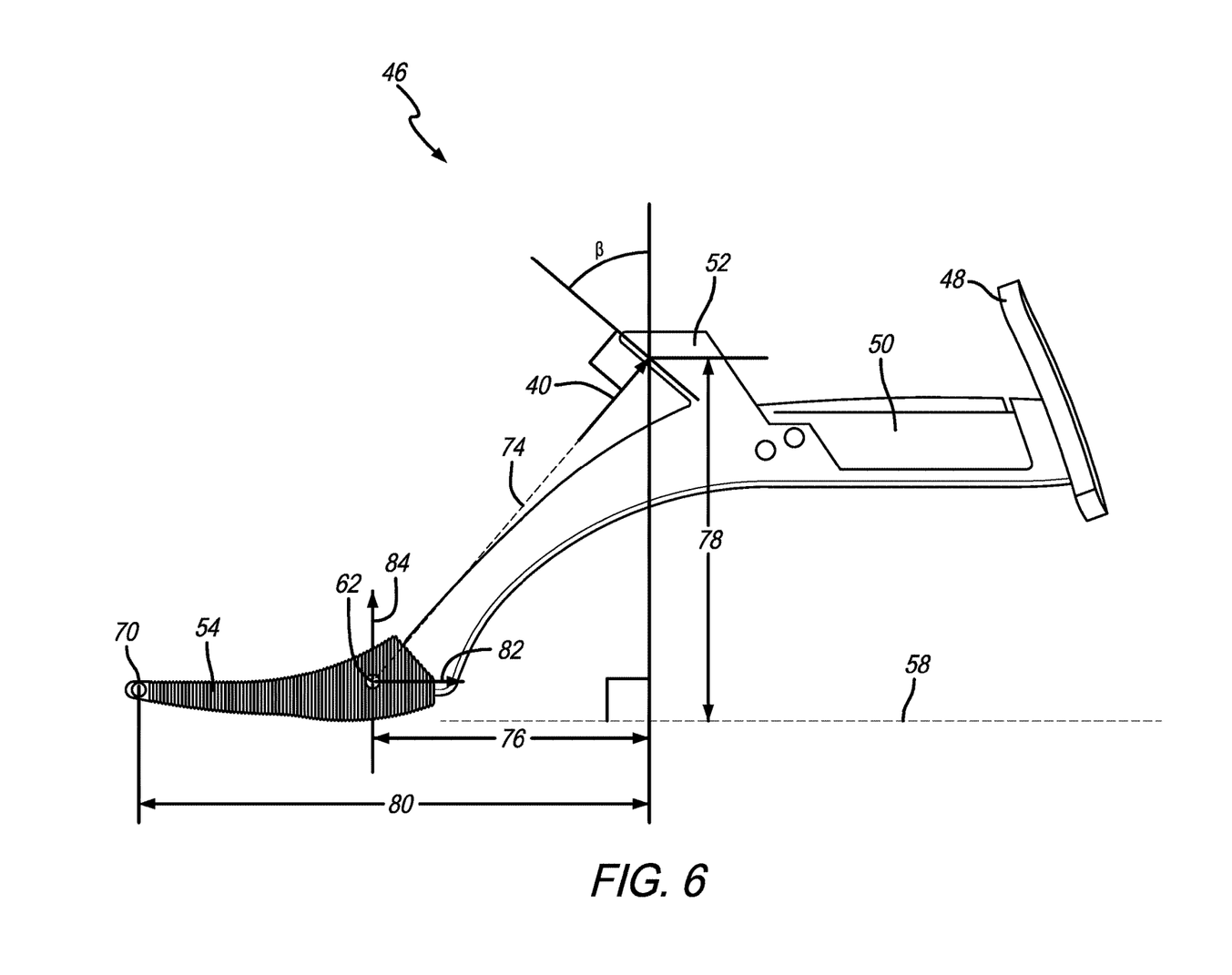
FIG. 6 is a side perspective view of the broach holder tool with reduced rasp moment similar to FIGS. 4 and 5, further illustrating applying a force to the withdrawal plate without substantial creation of a moment at the rasp.
Figure 7:
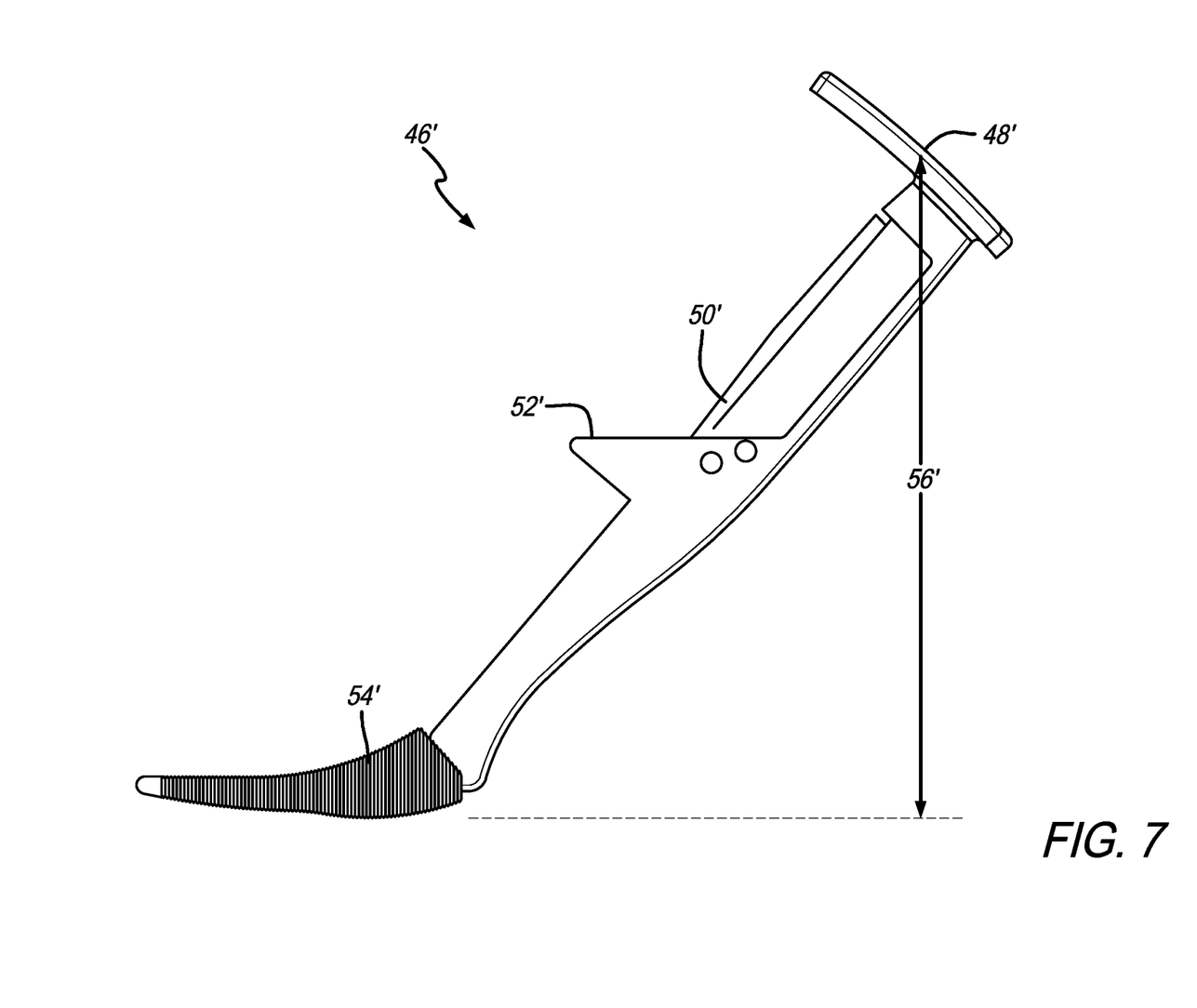
FIG. 7 is a side perspective view of an alternative broach holder tool with reduced rasp moment having a gain relatively larger than the gain shown with respect to the broach holder tool with reduced rasp moment in FIGS. 4-6.
Figure 8:
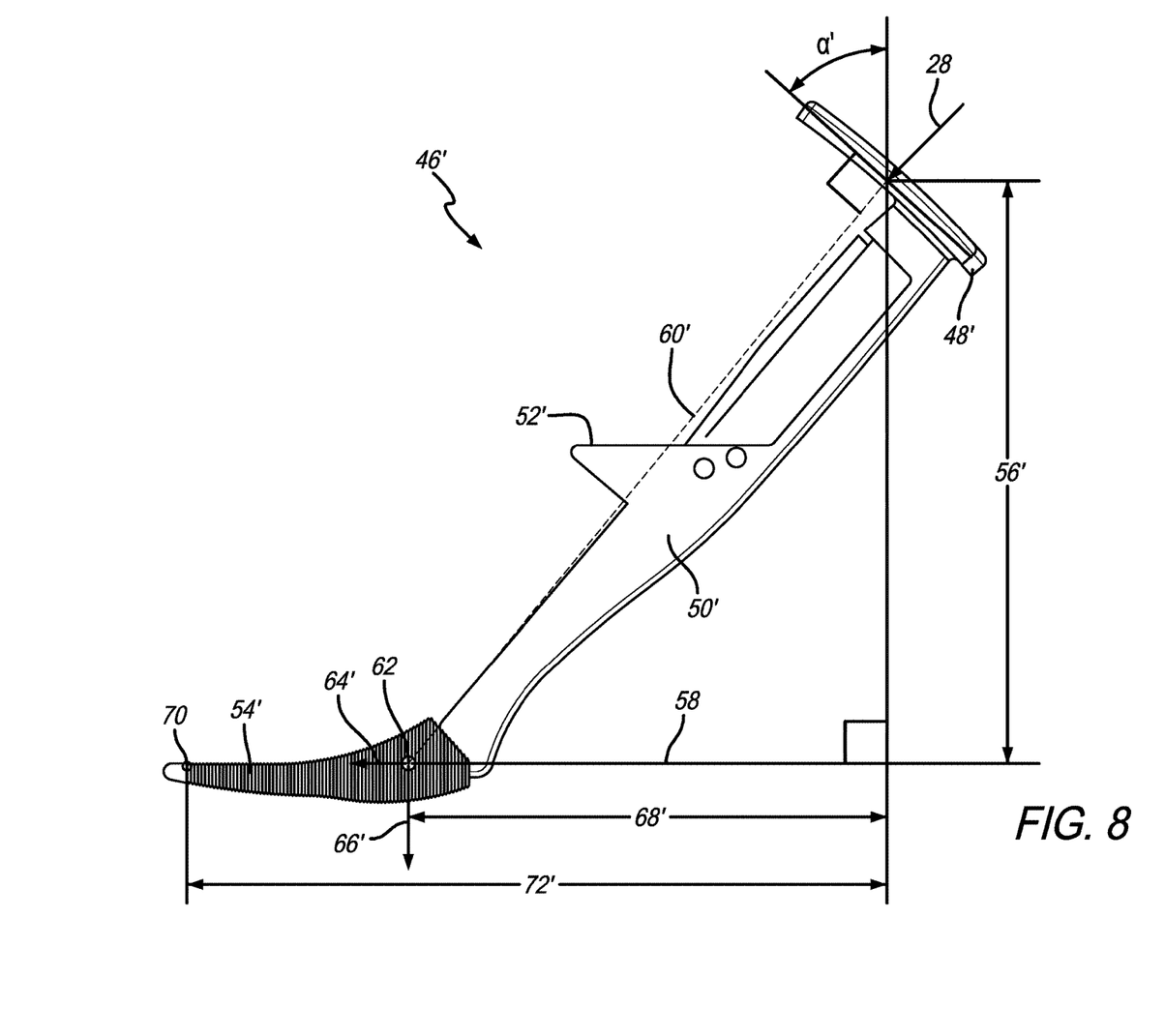
FIG. 8 is a side perspective view of the relatively larger gain broach holder tool with reduced rasp moment similar to FIG. 7, further illustrating applying a force to the strike plate without substantial creation of a moment at the rasp.
Figure 9:
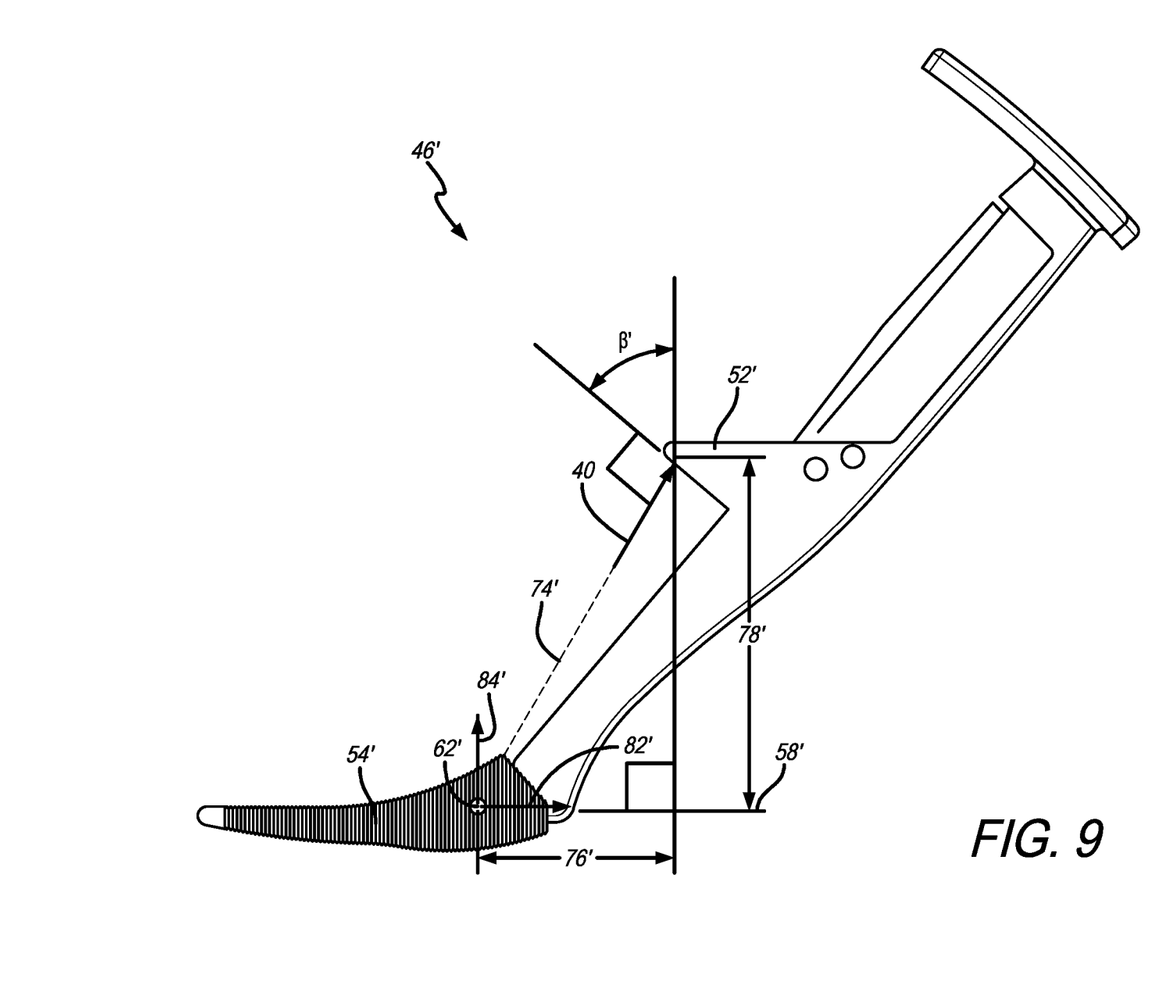
FIG. 9 is a side perspective view of the relatively larger gain broach holder tool with reduced rasp moment similar to FIGS. 7 and 8, further illustrating applying a force to the withdrawal plate without substantial creation of a moment at the rasp.

As shown in the exemplary drawings for purposes of illustration, a broach holder tool with reduced rasp moment is shown generally in FIGS. 4-6 by reference numeral 46 and an alternative broach holder tool with reduced rasp moment incorporating a relatively larger gain is shown in FIGS. 7-9 with respect to reference numeral 46'. First, with respect to FIGS. 4-6, the broach holder tool with reduced rasp moment 46 includes an angled strike plate 48, a generally S-shaped body or section 50 having an angled withdrawal plate 52 extending out therefrom, as shown, and an attachment mechanism (not shown) configured to selectively receive and retain a rasp 54. The attachment mechanism is preferably configured to selectively couple to multiple rasps that vary in size, shape, and/or configuration, depending on the needs during surgery (e.g., larger rasps may be needed as the intramedullary canal is sized for insertion of the prosthetic stem). In the embodiment shown in FIG. 4, the broach holder tool with reduced rasp moment 46 may include a gain or vertical 56 of about 3.5" relative to a horizontal 58. That is, the body of the section 50 carrying the angled strike plate 48 and/or the angled withdrawal plate 52 may be generally vertically offset relative to the position of the rasp 54 by the gain 56, which may provide enhanced angular orientation and insertion of the broach holder tool with reduced rasp moment 46 during anterior total hip replacement. In this respect, the broach holder tool 46 allows the surgeon to place the rasp 54 at the point of the intramedullary canal while positioning the angled strike plate 48 and/or the angled withdrawal plate 52 away from the body of the patient. This advantageously allows the surgeon to more easily access the angled strike plate 48 and/or the angled withdrawal plate 52 during surgery. But, as mentioned above, such offset positioning generates a moment along the rasp in prior art devices and typically near the point of entry, as shown in FIG. 1 (counterclockwise moment) with respect to applying the strike force 28 to the strike plate 22 and in FIG. 2 (clockwise moment) with respect to applying the withdrawal force 40 to the withdrawal plate 38. The withdrawal force 40 can alternatively be applied to the backside of the strike plate, as mentioned above with respect to FIG. 2, depending on surgeon preference.

As more specifically shown in FIG. 5, the angular strike plate 48 is offset from a normal perpendicular plane (see e.g., FIGS. 1 and 2) by an offset angle $\alpha$. In this respect, the offset angle $\alpha$ corresponds to directionally positioning the strike force 28 so that it follows an angled directional strike line 60 extending through a drive point 62 along the length of the rasp 54. The strike line 60 extends generally perpendicular to the strike plate 48 and forward from the strike force 28 as illustrated best in FIG. 5. Also, in the embodiment shown in FIG. 5, the drive point 62 is approximately where the rasp 54 couples to the section 50. Although, preferably, the drive point 62 is at a point along the length of the rasp 54 where the rasp 54 has a tendency to experience the greatest resistance while rasping the intramedullary canal. In an ideal condition, the broach holder tool 46 generates no moment at the drive point 62 because the strike force 28 translates through the drive point 62, as opposed to being applied to a moment arm extending from the drive point 62, as mentioned above. The location of the drive point 62 may change as the rasp 54 penetrates deeper into the canal or during removal, as described below, but for purposes of the present disclosure, the primary point of force translation will be described with respect to the approximate location of the drive point 62. To this end, there may be a number of factors that determine the location and size of a moment at or near the rasp 54. A person of ordinary skill in the art will recognize that the embodiments disclosed herein are advantageous over the prior art, such as the prior art broach holder tools 20, 20' discussed above, by way of substantially reducing (and possibly eliminating) the aforementioned moment because the strike line 60 extending from the strike plate 48 extends through the drive point 62 (or the point where the rasp 54 connects to the section 50), or within 5-10 degrees thereof, to minimize any moment within the rasp 54.

Translating the strike force 28 along the angled directional strike line 60 into the drive point 62 generates two vector forces thereon, a horizontal vector 64 and a vertical vector 66. In the embodiment disclosed in FIGS. 4-6, the horizontal vector 64 is of a greater magnitude than the vertical vector 66. Although, the size of each vector 64, 66 may change by differing the relative positioning of the strike plate 48 relative to the drive point 62. For example, decreasing an angular offset θ changes the magnitude of the force translated through the line 60 to the drive point 62 to be more horizontal in nature than vertical. As a result, this increases the amount of force translated into the horizontal vector 64 and decreases the amount of force translated into the vertical vector 66. In an ideal situation, as briefly mentioned above, the strike plate 28 is located along the horizontal 58 and perpendicular thereto so the strike force 28 translates only into the horizontal vector 64 for driving the rasp 54 straight down the intramedullary canal. In this example, the entire strike force 28 translates into energy driving the rasp 54 forward. But, due to the intricacies of total hip replacement surgery, for example, and especially so with respect to the anterior approach, this is not as feasible, especially when attempting to follow minimally invasive procedures. Thus, the broach holder tool 46 preferably includes some offset angle θ between the rasp 54 and the strike plate 48. Changing the offset angle θ changes each of the vectors 64,66 as described herein.

Additionally, the offset angle α may vary as a function of the height and length of the section 50. For example, in the embodiment illustrated in FIG. 5, decreasing the gain 56 results in the angled strike plate 48 being positioned at a lower height relative to the drive point 62. If the strike plate 48 remains oriented at the same angle α, then the strike line 60 perpendicular thereto would move upwardly and away from the drive point 62, thereby creating an unwanted moment, as described above with respect to FIGS. 1-3. Accordingly, the angular orientation of the strike plate 48 preferably changes so the strike force 28 applied perpendicular thereto drives through the strike line 60 directed into the drive point 62. Thus, decreasing the gain 56 requires decreasing the angle α and increasing the gain 56 requires increasing the angle α to maintain this relative relationship. In this respect, the desired angular offset of the strike plate 48 can be determined as a function of a horizontal distance 68 and the gain 56, and specifically by the formula: α=90−arctan (X/Y), where X is the horizontal distance 68 and Y is the vertical distance denoted by the gain 56. In the example shown in FIG. 5, assuming the horizontal distance 68 is approximately twice the distance of the gain 56 (i.e., X=2Y), the formula changes to α=90−arctan (2Y/Y), wherein α=~26.57°. Accordingly, in this embodiment, it is preferred that the angled strike plate 48 be offset from the vertical by approximately 26.57° to maintain the strike line 60 in line with the drive point 62.

Additionally, the surface of the strike plate may be further optimized to maintain the angle α. In one example, the strike plate surface may include a curved or spherical surface helps align the strike force 28 through the drive point 62. In this respect, the entire strike plate surface may have the curved or spheroidal surface or a portion of the strike plate surface may have the curved or spheroidal surface that has a radius centered, e.g., at the drive point 62.

As briefly mentioned above, the drive point 62 may vary along the length of the rasp 54. In some embodiments, the drive point 62 may be preferred to be in the position shown in FIG. 5, i.e., at the point where the rasp 54 attaches to the section 50. In other embodiments, the drive point 62 may be at a different point along the length of the rasp 54, along the S-shaped section 50 or at another point as needed and/or desired to reduce the moment forces applied to the intramedullary canal during rasping. For example, moving the drive point 62 to the end of the rasp 54, such as at point 70, may lengthen the horizontal to a distance 72 that is relatively three times longer than the gain 56. As such, the formula changes to α=90−arctan (3Y/Y), wherein α=~18.43°.

The same principles apply with respect to the withdrawal plate 52, as more specifically shown in FIG. 6. Here, the withdrawal force 40 is applied generally perpendicular to the angled withdrawal plate 52 so that a withdrawal line 74 extends through the drive point 62. Similar to the above, a withdrawal plate offset angle β is calculated by the formula β=90−arctan (A/B), where A is a horizontal distance 76 between the drive point 62 and the point of impact on the angled withdrawal plate 52, and B is a vertical distance 78 between the horizontal 58 and the point of impact on the angled withdrawal plate 52. In this case, while not necessarily drawn to scale, assuming the vertical distance 78 is approximately relatively 1.5 times the length of the horizontal distance 76 (i.e., wherein B=1.5 A), the formula changes to: β=90−arctan (A/1.5 A), wherein β=~56.31°. Again, for illustrative purposes, moving the drive point 62 to the point 70 increases the horizontal distance to a distance 80. If the horizontal distance 80 (i.e., "A") is equal to the vertical distance 76 (i.e., "B"), then the formula changes to β=90−arctan (1), wherein β=45.00°. Accordingly, the withdrawal plate 52 should be oriented at a general 45° angle relative to the vertical to ensure that the withdrawal force 40 is aligned along the withdrawal line 74 extending through the point 70. Aligning the withdrawal force to the desired drive point can also be accomplished with the design on the back side of the strike plate 48, as mentioned above with respect to FIG. 2, to allow for surgeon accessibility.

In one embodiment, the angular orientation of the angled strike plate 48 (i.e., angle α) and/or the angled withdrawal plate 52 (i.e., the withdrawal plate offset angle β) may be adjustable. For example, at the beginning of rasping the intramedullary canal, it may be that the desired drive point is closer to point 70 as opposed to point 62. As such, the surgeon may have the option of selectively positioning the angle α at a first angular offset that is relatively smaller than a second angular offset later on in the procedure as the drive point moves closer to point 62, and vice versa with respect to the withdrawal plate offset angle β, as the broach holder tool 46 is withdrawn from the intramedullary canal. Here, the angled strike plate 48 may pivot or rotate relative to the section 50, such as by lock-step engagement.

An alternative embodiment of the broach holder tool with reduced rasp moment 46' is illustrated with respect to FIGS. 7-9. Here, the broach holder tool 46' includes an alternative section 50' having a more linear construction when compared to the more S-shaped section 50 described above. Moreover, the broach holder tool 46' is shown including a gain 56' relatively longer than the gain 56 described above with respect to the broach holder tool 46, and may be as much as 8". Despite these above differences, the principles of angularly positioning an angled strike plate 48' and/or an angled withdrawal plate 52' are generally the same.

More specifically in this respect, FIG. 8 illustrates application of the strike force 28 generally perpendicular to the angled strike plate 48' and along a strike line 60', which happens to generally follow the length of the structure of the section 50' in this embodiment. As such, for translating the strike force 28 through a drive point 62' along a rasp 54', as indicated in FIG. 8, the strike plate 48' must be offset from the vertical by an offset angle α'. The offset angle α' is calculated by α'=90−arctan (X'/Y'), where X' is the horizontal distance 68' and the Y' is the vertical distance or gain 56'. In this embodiment, the vertical distance or gain 56' is approximately 1.25 times longer than the horizontal distance 68'. As such, Y'=1.25X'. Accordingly, this changes the formula to α'=90−arctan (X'/1.25X'), or ~51.34°. When comparing the two embodiments disclosed herein, FIG. 5 illustrates α=~26.57° and FIG. 8 illustrates α'=~51.34°. The difference in the offset angle α, α' is then represented by the difference in the magnitude of the force vectors applied at the drive point 62, namely the horizontal vector 64 of FIG. 5 is relatively larger than the horizontal vector 64' of FIG. 8, and the vertical vector 66 of FIG. 5 is relatively smaller than the vertical vector 66' of FIG. 8. This is because of the increased offset angle, which drives more of the force downwardly in FIG. 8 so the strike line 60 extends through the drive point 62, as opposed to some point offset therefrom, which may create an undesired moment. Of course, as described above, the drive point 62 could be moved along the length of the rasp 54, depending on the desired drive point characteristics. So, in another aspect of FIG. 8, moving the drive point to point 70 increases the horizontal distance 68' to a distance 72', which generally increases the ratio of the distance along the horizontal 58 relative to the vertical distance or gain 56'. A larger ratio results in a smaller offset angle α', and vice versa. Moreover, a smaller offset angle α' is associated with an increased ratio of the horizontal vector 64' relative to the vertical vector 66', and vice versa.

FIG. 9 illustrates application of the angled withdrawal plate 52' in association with the broach holder tool with reduced rasp moment 46' as disclosed herein. More specifically, as described above, the angled withdrawal plate 52' is preferably formed perpendicular to the withdrawal force 40 applied thereto when removing the broach holder tool 46' from the intramedullary canal during rasping. The withdrawal force 40 is preferably aligned along a withdrawal line 74' that intersects the drive point 62' as shown in FIG. 9. Thus, as described above with respect to the withdrawal plate 52 of FIG. 6, the withdrawal offset angle β' is calculated by the formula β'=arctan (A'/B'), where A' is the horizontal distance 76' and B' is the vertical distance 78'. In this embodiment, while again not necessarily being drawn to scale, the vertical distance 78' (i.e., "B") may be 1.75 times longer than the horizontal distance 76' (i.e., "A"). As such, B=1.75 A, and the formula changes to β'=arctan (A'/1.75 A'), wherein β'=~60.26°.

Additionally, the magnitude of each of a horizontal vector 82' and a vertical vector 84' changes, depending on the offset angle β'. For example, if the offset angle β'=45.00°, then the horizontal vector 82' would be equal to the vertical vector 84'. Increasing the offset angle β' to a larger angle, such as to 60.26° as mentioned above, results in an increase in the vertical vector 84' relative to the magnitude of the horizontal vector 82', and vice versa. Accordingly, the positioning of the angled strike plate 48, 48' and/or the angled withdrawal plate 52, 52' can be used to reduce the stress on the proximal femur during surgery.

There may be a need for some broach holder tools to have an offset in another plane, other than what is shown in FIGS. 4-9, such as in the horizontal plate as shown and described above with respect to FIGS. 3A and 3B. Such a broach holder tool may be needed to facilitate increased access due to surgical approach or obstructions due to patient anatomy. Similar principles as described above with respect to FIGS. 4-9 could be followed in all planes to ensure alignment of the strike force with some drive point along the length of the rasp.

Although several embodiments have been described in detail for purposes of illustration, various modifications may be made without departing from the scope and spirit of the invention. Accordingly, the invention is not to be limited, except as by the appended claims.

What is claimed is:

1. A broach holder tool with a reduced rasp moment, comprising:
   a generally elongated and rigid broach holder body having a size and shape to facilitate broaching of a bone;
   a rasp selectively coupled to a first end of the broach holder body; and
   an angled strike plate coupled a second end of the broach holder body opposite the rasp, wherein the angled strike plate includes a spherical strike surface configured to receive a strike force perpendicular thereto that translates along a strike line aligned with and extending through a drive point of the rasp where the rasp is configured to enter the bone, wherein a center point of the spherical strike surface is aligned with the drive point along the strike line thereby producing an axial force into the bone while substantially reducing the rasp moment.

2. The broach holder tool of claim 1, wherein the angled strike plate is offset from a long axis of the broach holder body by a vertical offset angle α comprising 10-30 degrees.

3. The broach holder tool of claim 2, wherein the vertical offset angle α is defined by the formula: α=90−arctan (X/Y), where X comprises a horizontal distance between the drive point and where the strike force contacts the spherical strike surface and Y comprises a vertical gain between the drive point and where the strike force contacts the spherical strike surface.

4. The broach holder tool of claim 3, wherein decreasing the vertical gain decreases the vertical offset angle α and wherein increasing the vertical gain increases the vertical offset angle α.

5. The broach holder tool of claim 3, wherein a substantially horizontal insertion force at the rasp increases by decreasing the vertical gain and the substantially horizontal insertion force at the rasp decreases by increasing the vertical gain, while maintaining the reduced rasp moment.

6. The broach holder tool of claim 1, further including an angled withdrawal plate coupled to the broach holder body between the rasp and the angled strike plate, the angled withdrawal plate including a spherical withdrawal surface configured to receive a withdrawal force perpendicular thereto that translates substantially along an angled directional withdrawal line extending through a withdrawal point where the rasp is configured to be removed from the bone after broaching.

7. The broach holder tool of claim 6, wherein the angled withdrawal plate is offset from a long axis of the broach holder body by a vertical offset angle β defined by the formula: β=90−arctan (A/B), where A comprises a horizontal distance between the withdrawal point and where the withdrawal force contacts the spherical withdrawal surface of the angled withdrawal plate and B comprises a vertical distance between the withdrawal point and where the withdrawal force contacts the spherical withdrawal surface of the angled withdrawal plate.

8. The broach holder tool of claim 1, wherein the angled strike plate comprises an adjustable angled strike plate selectively positionable relative to the drive point.

9. The broach holder tool of claim 1, wherein the broach holder body comprises an S-shape.

10. The broach holder tool of claim 1, wherein the rasp is selectively interchangeable.

11. A broach holder tool with a reduced rasp moment, comprising:

a generally elongated and rigid broach holder body having a size and shape to facilitate broaching of an intramedullary canal in a bone in preparation for implantation of a prosthetic femoral stem;

a selectively interchangeable rasp coupled to a first end of the broach holder body;

an angled strike plate coupled to a second end of the broach holder body opposite the rasp wherein the angled strike plate comprises a strike surface configured to receive a strike force perpendicular thereto, that translates along a strike line aligned with and extending through a drive point of the rasp where the rasp is configured to enter the bone, wherein a center point of the strike surface is aligned with the drive point along the strike line thereby producing an axial force into the bone while substantially reducing the rasp moment; and an angled withdrawal plate coupled to the broach holder body between the rasp and the angled strike plate, the angled withdrawal plate including a spherical withdrawal surface.

12. The broach holder tool of claim 11, wherein the angled withdrawal plate is offset from a long axis of the broach holder body by a vertical offset angle $\beta$ comprising 10-30 degrees.

13. The broach holder tool of claim 12, wherein the vertical offset angle $\beta$ is defined by the formula: $\beta=90-\arctan(A/B)$, where A comprises a horizontal distance between a withdrawal point of the rasp and the spherical withdrawal surface and B comprises a vertical distance between the withdrawal point of the rasp and the spherical withdrawal surface.

14. The broach holder tool of claim 11, wherein the angled withdrawal plate comprises an adjustable angled withdrawal plate selectively positionable relative to the withdrawal point of the rasp.

15. The broach holder tool of claim 11, wherein the angled strike plate is offset from a long axis of the broach holder body by a vertical offset angle $\alpha$ defined by the formula: $\alpha=90-\arctan(X/Y)$, where X comprises a horizontal distance between the drive point and where the strike force contacts the strike surface of the angled strike plate and Y comprises a vertical gain between the drive point and where the strike force contacts the strike surface of the angled strike plate.

16. A broach holder tool with a reduced rasp moment, comprising:

a generally elongated and rigid broach holder body having a size and shape to facilitate broaching of a bone;

a rasp selectively coupled to a first end of the broach holder body;

an angled strike plate coupled to a second end of the broach holder body opposite the rasp and having a spherical strike surface configured to receive a strike force perpendicular thereto that translates along a strike line aligned with and extending through a drive point of the rasp where the rasp is configured to enter the bone, the spherical strike surface being offset from a long axis of the broach holder body by a vertical offset angle $\alpha$ comprising 10-30 degrees, and wherein a center point of the strike surface is aligned with the drive point along the strike line within a maximum deviation of 10 degrees, thereby producing an axial force into the bone while substantially reducing the rasp moment; and an angled withdrawal plate extending out from the broach holder body between the rasp and the angled strike plate and including a spherical withdrawal surface.

17. The broach holder tool of claim 16, wherein the vertical offset angle $\alpha$ is defined by the formula: $\alpha=90-\arctan(X/Y)$, where X comprises a horizontal distance between the drive point and where the strike force contacts the spherical strike surface and Y comprises a vertical gain between the drive point and where the strike force contacts the spherical strike surface; and wherein the angled withdrawal plate includes a vertical offset angle $\beta$ defined by the formula: $\beta=90-\arctan(A/B)$, where A comprises a horizontal distance between a withdrawal point of the rasp and where the withdrawal force contacts the spherical withdrawal surface and B comprises a vertical distance between the withdrawal point of the rasp and where the withdrawal force contacts the spherical withdrawal surface.

18. The broach holder tool of claim 16, wherein the broach holder body comprises an S-shape and wherein decreasing the vertical gain decreases the vertical offset angle $\alpha$ and increases a substantially horizontal insertion force at the rasp and wherein increasing the vertical gain increases the vertical offset angle $\alpha$ and decreases the substantially horizontal insertion force at the rasp.

19. The broach holder tool of claim 16, wherein the angled strike plate is selectively positionable relative to the drive point along a selectively interchangeable rasp.

20. A broach holder tool with a reduced rasp moment, comprising:

a generally elongated and rigid broach holder body having a size and shape to facilitate broaching of a bone;

a rasp selectively coupled to a first end of the broach holder body;

an angled strike plate coupled to a second end of the broach holder body opposite the rasp and having a spherical strike surface configured to receive a strike force perpendicular thereto that translates along a strike line aligned with and extending through a drive point of the rasp where the rasp is configured to enter the bone, the spherical strike surface being offset from a long axis of the broach holder body by a vertical offset angle $\alpha$ comprising 10-30 degrees, and wherein a center point of the strike surface is aligned with the drive point along the strike line within a maximum deviation of 10 degrees, thereby producing an axial force into the bone while substantially reducing the rasp moment; and an angled withdrawal plate extending out from the broach holder body between the rasp and the angled strike plate and including a spherical withdrawal surface, the angled withdrawal plate being offset from a long axis of the broach holder body by an offset angle $\beta$ comprising 10-30 degrees.

* * * * *